United States Patent
Yamashita (10) Patent No.: US 9,155,457 B2
(45) Date of Patent: Oct. 13, 2015

(54) ENDOSCOPE APPARATUS FOR PERFORMING COLOR CORRECTION

(71) Applicant: OLYMPUS MEDICAL SYSTEMS CORP., Tokyo (JP)

(72) Inventor: Shinji Yamashita, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 17 days.

(21) Appl. No.: 14/159,666

(22) Filed: Jan. 21, 2014

(65) Prior Publication Data

US 2014/0180004 A1 Jun. 26, 2014

Related U.S. Application Data

(63) Continuation of application No. PCT/JP2013/067075, filed on Jun. 21, 2013.

(30) Foreign Application Priority Data

Aug. 1, 2012 (JP) ................................. 2012-171338

(51) Int. Cl.
*A61B 1/06* (2006.01)
*A61B 1/04* (2006.01)
(Continued)

(52) U.S. Cl.
CPC .............. *A61B 1/043* (2013.01); *A61B 1/00006* (2013.01); *A61B 1/00009* (2013.01);
(Continued)

(58) Field of Classification Search
CPC .......... A61B 1/06; A61B 1/0638; A61B 1/04; A61B 1/043; A61B 1/045; A61B 1/05; A61B 1/00009; A61B 1/0661; A61B 1/0684

USPC ......... 600/102, 109, 117, 160, 178, 179, 180; 348/68, 69, 70

See application file for complete search history.

(56) References Cited

U.S. PATENT DOCUMENTS 8,540,626 B2 * 9/2013 Seto et al. ...................... 600/178
8,550,990 B2 * 10/2013 Seto et al. ...................... 600/180
(Continued)

FOREIGN PATENT DOCUMENTS

| EP | 2 030 559 A1 | 3/2009 |
|---|---|---|
| JP | 2009-056248 A | 3/2009 |

(Continued)

OTHER PUBLICATIONS

International Search Report dated Aug. 13, 2013 issued in PCT/JP2013/067075.

*Primary Examiner* — Anhtuan T Nguyen
*Assistant Examiner* — William Chou
(74) *Attorney, Agent, or Firm* — Scully, Scott, Murphy & Presser, PC (57) ABSTRACT

An endoscope apparatus includes a white LED that emits synthesized light of the excitation light and the fluorescence, a CCD that picks up an image of an observation part, a brightness detecting section that detects brightness of an optical image of the observation part based on an image pickup signal outputted by the CCD, a light adjusting circuit that adjusts driving time of the semiconductor light source, a color correction parameter deriving section that derives a first color correction parameter for correcting a gain of a color component signal related to the excitation light in a video signal, and a second color correction parameter for correcting a gain of a color component signal related to the fluorescence, and a color tone varying section that corrects the excitation-light-related gain with the first color correction parameter, and corrects fluorescence-related gain with the second color correction parameter.

5 Claims, 4 Drawing Sheets

(51) Int. Cl.
*A61B 1/00* (2006.01)
*A61B 1/05* (2006.01)
*A61B 1/07* (2006.01)
*G02B 23/24* (2006.01)

(52) U.S. Cl.
CPC ............... *A61B 1/05* (2013.01); *A61B 1/0638* (2013.01); *A61B 1/0653* (2013.01); *A61B 1/0684* (2013.01); *A61B 1/07* (2013.01); *G02B 23/2484* (2013.01); *G02B 23/2469* (2013.01)

(56) References Cited

U.S. PATENT DOCUMENTS

| | | | | |
|---|---|---|---|---|
| 8,553,077 B2 * | 10/2013 | Ozawa et al. | .................. | 348/68 |
| 8,564,651 B2 * | 10/2013 | Ozawa et al. | .................. | 348/68 |
| 8,624,966 B2 * | 1/2014 | Ozawa et al. | .................. | 348/68 |
| 8,858,429 B2 * | 10/2014 | Mizuyoshi et al. | .......... | 600/180 |
| 2009/0062617 A1 | 3/2009 | Mizuyoshi | | |
| 2011/0034770 A1 * | 2/2011 | Endo et al. | .................... | 600/118 |
| 2011/0257483 A1 * | 10/2011 | Mizuyoshi et al. | .......... | 600/178 |
| 2011/0257484 A1 * | 10/2011 | Mizuyoshi et al. | .......... | 600/178 |
| 2012/0078046 A1 | 3/2012 | Sasaki et al. | | |

FOREIGN PATENT DOCUMENTS

| | | |
|---|---|---|
| JP | 2011-067267 A | 4/2011 |
| JP | 2012-070935 A | 4/2012 |

* cited by examiner

ENDOSCOPE APPARATUS FOR PERFORMING COLOR CORRECTION

CROSS REFERENCE TO RELATED APPLICATION

This application is a continuation application of PCT/JP2013/067075 filed on Jun. 21, 2013 and claims benefit of Japanese Application No. 2012-171338 filed in Japan on Aug. 1, 2012, the entire contents of which are incorporated herein by this reference.

BACKGROUND OF THE INVENTION

1. Field of the Invention

The present invention relates to an endoscope apparatus and in particular to an endoscope apparatus for performing color correction in accordance with driving time of a light source section.

2. Description of the Related Art

Conventionally, an endoscope apparatus comprises an endoscope having an image pickup device such as a CCD for picking up an image of a subject inside a living body, a light source integrated type processor including a light source such as an LED that supplies illumination light for illuminating the subject to the endoscope and a processor that converts an image pickup signal picked up by the CCD into a video signal and outputs the video signal, and a monitor that displays an image according to the video signal outputted from the light source integrated type processor.

Further, in recent years, a light source has been put into practice that forms illumination light of a desired color, using a light emitting source that emits excitation light and a fluorescent substance that emits fluorescence having a color (wavelength) different from a color of the excitation light by being exited by the excitation light, by combining the fluorescence from the fluorescent substance and excitation light that has transmitted through the fluorescent substance without being absorbed by the fluorescent substance, as a light source for supplying illumination light to a subject. For example, in Japanese Patent Laid-Open Publication No. 2011-67267, there is disclosed an endoscope apparatus which, by using a blue light laser source that emits blue laser light and a fluorescent substance that absorbs a part of energy of the blue laser light and emits green-yellow fluorescent light, forms white illumination light using green-yellow fluorescent light by the fluorescent substance and blue laser light that has transmitted through the fluorescent substance without being absorbed by the fluorescent substance.

In such an endoscope apparatus which forms illumination light of a desired color using the light emitting source that emits the excitation light and the fluorescent substance, a wavelength and emission strength of the excitation light emitted from the light emitting source changes in accordance with elapse of time from a start of use of the light emitting source to lose a color balance of the illumination light. Therefore, in the endoscope apparatus, a chromaticity correction table which is necessary for correction processing of adjusting an image signal to have a proper chromaticity is stored in advance and the color correction processing is performed with respect to the image signal based on correction data stored in the chromaticity correction table.

Incidentally, in such an endoscope, light adjustment for adjusting an amount of the illumination light is performed at the light source and is realized, for example, by the PWM (pulse width modulation) for performing variable control of a pulse width (driving time) which is a width of a pulse supplied to the light emitting source and during which the light emitting source is turned on while keeping a current value constant, or the variable current for performing variable control of a value of a current to be supplied to the light emitting source.

Further, there is an endoscope apparatus which performs the light adjustment using an electronic shutter of an image pickup device without performing the light adjustment at the light source, but a circuit scale of the image pickup device is increased if an electronic shutter function is equipped. In general, in the endoscope apparatus, it is necessary to downsize the image pickup device arranged at a distal end of an insertion portion in order to reduce a diameter of the insertion portion of the endoscope, and therefore an image pickup device not equipped with the electronic shutter function is used.

SUMMARY OF THE INVENTION

An endoscope apparatus according to an aspect of the present invention includes: a light source section that includes a semiconductor light source that emits excitation light and a fluorescent substance that emits fluorescence by being excited by the excitation light, and emits synthesized light of the excitation light and the fluorescence; an image pickup section that picks up an image of an observation part illuminated by the illumination light; a brightness detecting section that detects brightness of an optical image of the observation part based on an image pickup signal outputted by the image pickup section; a light source control section that adjusts driving time of the semiconductor light source in each image pickup period of the image pickup section based on a detection result of the brightness detecting section; a color correction parameter deriving section that derives a first color correction parameter for correcting a gain of a color component signal related to the excitation light in a video signal generated by image pickup by the image pickup section, and a second color correction parameter for correcting a gain of a color component signal related to the fluorescence; and a color correcting section that performs color correction by correcting the gain of the color component signal related to the excitation light with the first color correction parameter, and correcting the gain of the color component signal related to the fluorescence with the second color correction parameter.

DETAILED DESCRIPTION OF THE PREFERRED EMBODIMENTS

Hereinafter, an embodiment of the present invention will be explained in detail referring to the drawings.

First, a configuration of an endoscope apparatus according to the embodiment of the present invention will be explained based on FIG. 1.

Figure 1:
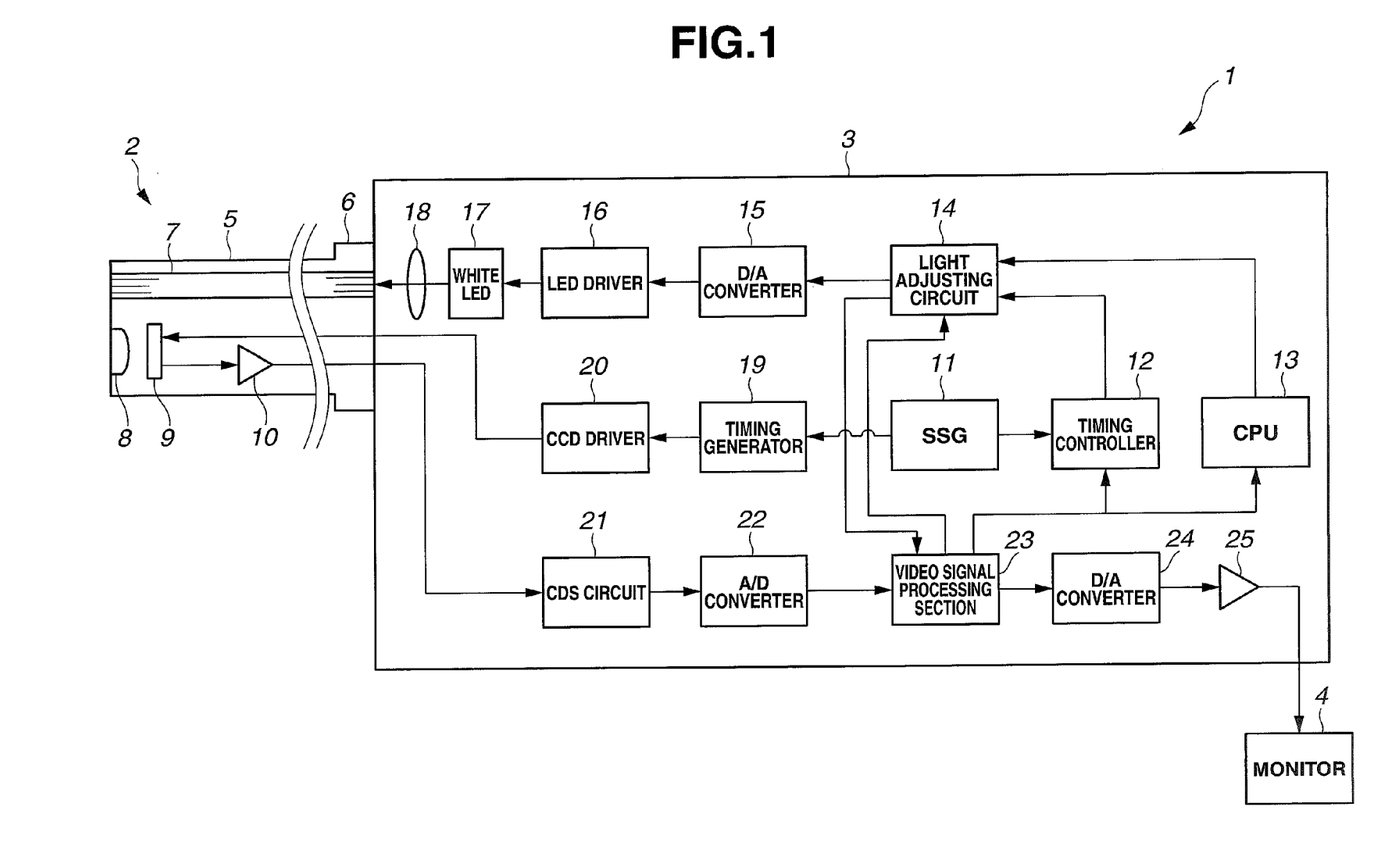
FIG. 1 is a configuration diagram showing a configuration of an endoscope apparatus according to an embodiment of the present invention.

FIG. 1 is a configuration diagram showing the configuration of the endoscope apparatus according to the embodiment of the present invention.

As shown in FIG. 1, an endoscope apparatus 1 is configured to include an endoscope 2 that picks up an image of a subject inside a living body and outputs an image pickup signal, a light source incorporated processor (hereinafter referred to simply as a processor) 3 integrally provided with a light source that supplies illumination light for illuminating the subject to the endoscope 2 and a processor that converts the image pickup signal outputted from the endoscope 2 into a video signal and outputs the video signal, and a monitor 4 that displays an image in accordance with the video signal outputted from the processor 3. It is noted that the light source that supplies the illumination light to the endoscope 2 and the processor that converts the image pickup signal into the video signal and outputs the video signal may be separately provided.

The endoscope 2 includes an insertion portion 5 that is elongated and flexible, and insertable into the living body. Further, the endoscope 2 includes an operation portion, not shown, that is formed at a rear end of the insertion portion 5 and a universal cable that extends from the operation portion. The endoscope 2 is configured to be attachable to and detachable from the processor 3 by a connector 6 provided at an end of the universal cable.

A light guide 7 is inserted inside the insertion portion 5. An end face of the light guide 7 on a light emitting side is arranged on a distal end face of the insertion portion 5. Further, an end face of the light guide 7 on a light entering side is arranged inside the connector 6.

Thus, according to the above configuration, the illumination light emitted from the processor 3 is transmitted through the light guide 7 when the connector 6 and the processor 3 are connected, and is emitted forward from the distal end face of the insertion portion 5 and illuminates the subject inside the living body.

On the distal end face of the insertion portion 5, there is provided an objective lens 8 that forms an optical image of the subject illuminated by the illumination light emitted from the light guide 7. At an image forming position of the objective lens 8, a CCD 9 is provided as an image pickup device. Besides, the present embodiment is configured by using the CCD 9 as the image pickup device, but it is not limited to this configuration and may be configured by using a CMOS, etc.

The CCD 9 as an image pickup portion performs photoelectric conversion on return light from the subject that has been subjected to image forming by the objective lens, based on a CCD drive signal from a CCD driver 20 as described later, to obtain an image pickup signal. The image pickup signal outputted from the CCD 9 is amplified by an amplifier 10 provided inside the insertion portion 5, and then inputted to a CDS circuit 21 as described later.

The processor 3 is configured to include a sync signal generator (hereinafter referred to as SSG) 11, a timing controller 12, a CPU 13, a light adjusting circuit 14, a D/A converter 15, an LED driver 16, a white LED 17, a condensing lens 18, a timing generator 19, a CCD driver 20, a CDS circuit 21, an A/D converter 22, a video signal processing section 23, a D/A converter 24 and an amplifier 25. Besides, whole or part of the configuration of the processor 3 may be provided in the endoscope 2. For example, it may be configured such that the white LED 17 is provided at the distal end of the insertion portion 5 of the endoscope 2 without providing the light guide 7, or the CDS circuit 21 and the A/D converter 22 are provided in the endoscope 2.

The SSG 11 generates a synchronous signal for synchronization in the entire apparatus, and outputs the signal to the timing controller 12 and the timing generator 19. The timing controller 12 generates a timing signal for PWM control based on the synchronous signal from the SSG 11 and outputs the generated signal to the light adjusting circuit 14.

The CPU 13 controls, in addition to the timing controller 12, the light adjusting circuit 14 and the video signal processing section 23, the entire apparatus. Further, when a user sets a brightness level by operating an operation portion, not shown, which is provided at the endoscope 2 or the processor 3, the CPU 13 outputs a setting signal of the brightness level in accordance with the set value.

To the light adjusting circuit 14, a luminance signal from the video signal processing section 23 is inputted in addition to the timing signal from the timing controller 12 and the setting signal of the brightness level from the CPU 13. The light adjusting circuit 14 generates a PWM signal having a predetermined pulse width for causing the white LED 17 to emit light of predetermined brightness based on the timing signal, the setting signal of the brightness level and the luminance signal inputted, and outputs the generated signal to the D/A converter 15. Further, the light adjusting circuit 14 outputs set value information of the pulse width of the PWM signal to the video signal processing section 23.

The D/A converter 15 performs D/A conversion, from a digital signal to an analog signal, of the PWM signal of the predetermined pulse width from the light adjusting circuit 14 and outputs the converted signal to the LED driver 16. The LED driver 16 drives the white LED 17 with the PWM signal of the predetermined pulse width which is outputted from the light adjusting circuit 14 and subjected to the D/A conversion.

The white LED 17 as the light source section is configured to include a blue LED as a light emitting section that emits blue light in accordance with the PWM signal from the LED driver 16, and a yellow fluorescent substance that is arranged on a light emitting side of the blue LED. The fluorescent substance is excited by the blue light (excitation light) from the blue LED and emits yellow fluorescence. Further, a part of the blue excitation light transmits through the fluorescent substance as it is. In this way, in the white LED 17, white light is formed by the blue excitation light which has transmitted through the fluorescent substance and the yellow fluorescence emitted from the fluorescent substance, and is emitted toward the condensing lens 18. Besides, the light emitting section is not limited to the white LED 17 constituted by the blue LED and the fluorescent substance, and may be configured to include a laser diode which emits a blue laser beam and a fluorescent substance. In addition, the illumination light emitted from the light source section is not limited to the white light, and further the color of the excitation light from the light emitting section and the color of the fluorescence from the fluorescent substance are not limited to blue and yellow, respectively, and the light source section may be one that emits illumination light of a color suitable for observation of the subject.

The condensing lens 18 condenses the white illumination light from the white LED 17 and supplies the condensed light to the end face of the light guide 7 on the light entering side. The illumination light supplied to the end face of the light guide 7 on the light entering side is transmitted through the light guide 7 and emitted forward from the distal end face of the insertion portion 5 to illuminate the subject inside the living body.

Besides, the white LED 17 may have separate configuration by being divided into the light emitting section that emits the excitation light and a fluorescent substance section provided with the fluorescent substance that emits fluorescence by the excitation light, which may be separately arranged. Further, only the fluorescent substance section may be provided at a front face of a light emitting end of the light guide 7 in the distal end of the insertion portion 5 of the endoscope 2, and the excitation light from the light emitting section may be transmitted to the fluorescent substance section by the light guide 7 to illuminate the subject by the illumination light from the fluorescent substance section.

The timing generator 19 generates a timing signal for controlling an exposure time period, read timing, etc. of the CCD 9 in accordance with the synchronous signal outputted from the SSG 11, and outputs the generated signal to the CCD driver 20.

The CCD driver 20 generates the CCD drive signal for driving the CCD 9 in accordance with the timing signal outputted from the timing generator 19, and outputs the generated signal to the CCD 9 to control the exposure time period, the read timing, etc. of the CCD 9. An image pickup signal read out from the CCD 9 in accordance with the CCD drive signal outputted from the CCD driver 20 is amplified by the amplifier 10, as described above, and then inputted to the CDS circuit 21.

The CDS circuit 21 performs correlated double sampling processing, extracts signal portions in the image pickup signal, and performs conversion into a baseband signal. The baseband signal is outputted to the A/D converter 22. The A/D converter 22 converts the baseband signal from the CDS circuit 21 into a digital signal and outputs the converted signal to the video signal processing section 23.

The video signal processing section 23 as a signal conversion section performs predetermined video signal processing such as gamma correction and enhance processing with respect to the digital signal from the A/D converter 22, the digital signal being converted into the video signal for display on the monitor 4. Further, the video signal processing section 23 outputs the video signal obtained by performing color correction processing, as described later, based on the set value information of the pulse width of the PWM signal from the light adjusting circuit 14, to the D/A converter 24.

The D/A converter 24 converts the video signal from the video signal processing section 23 into an analog signal, and outputs the converted signal to the amplifier 25. The amplifier 25 amplifies the video signal which is converted into the analog signal by the D/A converter 24, and outputs the amplified signal to the monitor 4. Thus, the monitor 4, as a display section, graphically displays a subject image picked up by the CCD 9.

Here, the relation between the pulse width of the PWM signal and the illumination light will be described.

Figure 2:
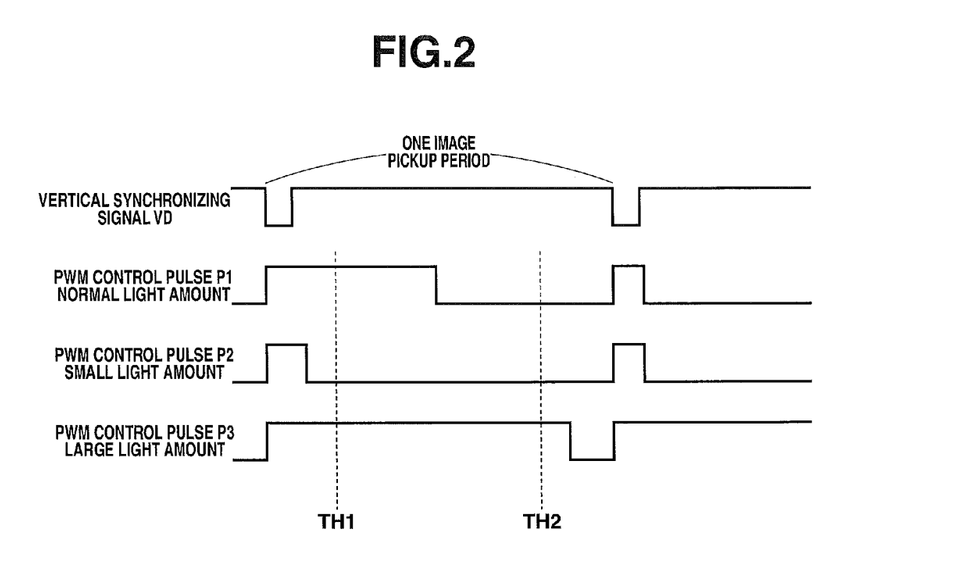
FIG. 2 is a diagram for explaining a pulse width of a PWM signal.
Figure 3:
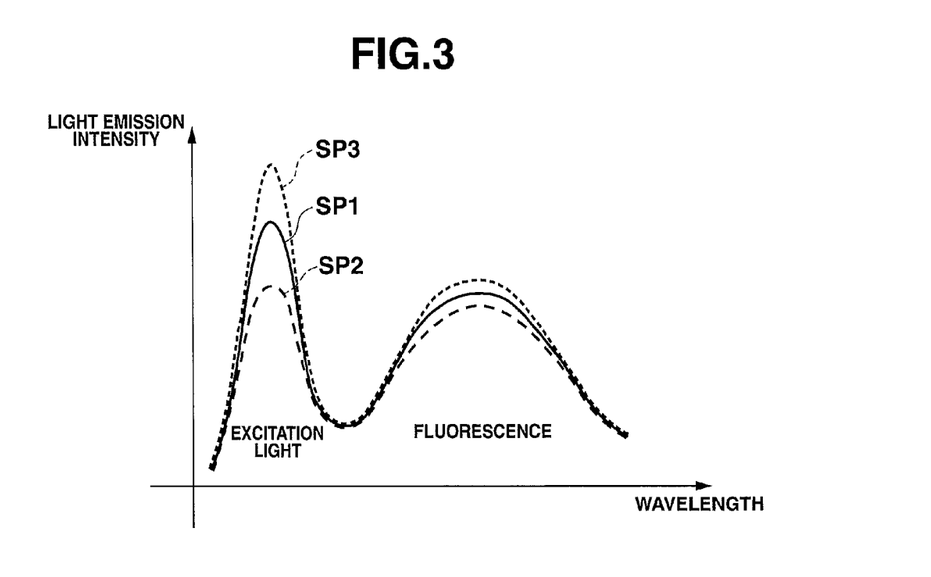
FIG. 3 is a diagram for explaining a spectrum of illumination light when causing a white LED 17 to emit light with the pulse width of the PWM signal of FIG. 2.

FIG. 2 is a diagram for explaining the pulse width of the PWM signal, and FIG. 3 is a diagram for explaining the spectrum of illumination light when causing the white LED 17 to emit light with the pulse width of the PWM signal of FIG. 2.

As shown in FIG. 2, the light adjusting circuit 14 as the light source control section controls brightness of the illumination light emitted from the white LED 17 by varying the pulse width of the PWM signal in every image pickup period of the CCD 9, that is, by adjusting driving time (ON/OFF time) of the white LED 17. In a case of performing observation with a normal light amount, the pulse width of the PWM signal is within a range wider than a first threshold TH1 and narrower than a second threshold TH2. In a case of a pulse P1 having the pulse width of the PWM signal wider than the first threshold TH1 and narrower than the second threshold TH2, a spectrum of the illumination light emitted from the white LED 17 in one image pickup period is a spectrum SP1 shown by the solid line in FIG. 3.

On the other hand, if a distal end portion of the insertion portion 5 is moved too close to the subject, the light adjusting circuit 14 makes the pulse width of the PWM signal narrower to reduce the light amount of the illumination light emitted from the white LED 17. In a case of a pulse P2 having the pulse width of the PWM signal equal or less than the first threshold TH1, a spectrum of the illumination light emitted from the white LED 17 in one image pickup period is a spectrum SP2 shown by the sparse broken line in FIG. 3. When the pulse width of the PWM signal becomes equal to or less than the first threshold TH1, light emission intensity of the blue excitation light which has transmitted through the fluorescent substance without irradiation thereto decreases with respect to the case of the pulse P1. In contrast, a decreasing rate of light emission intensity of the yellow fluorescence excited by the blue excitation light with respect to the case of the pulse P1 is lower than that of the blue excitation light which has transmitted through the fluorescent substance without irradiation thereto. Therefore, a relative ratio between the emission intensity of the excitation light which has transmitted through the fluorescent substance without irradiation and the emission intensity of the fluorescence emitted from the fluorescent substance, in one image pickup period, in the case of the pulse P1 differs from the relative ratio in the case of the pulse P2, i.e. the similarity between the spectrum of the illumination light in the case of the pulse P1 and the spectrum of the illumination light in the case of the pulse P2 is lost so that the color balance is lost.

Similarly, if the distal end portion of the insertion portion is moved away from the subject, the light adjusting circuit 14 broadens the pulse width of the PWM signal to increase the light amount of the illumination light that is emitted from the white LED 17. In the case of the pulse P3 having the pulse width of the PWM signal equal to or more than the second threshold TH2, the spectrum of the illumination light emitted from the white LED 17 in one image pickup period is a spectrum SP3 as shown by the broken line in FIG. 3. When the pulse width of the PWM signal becomes equal to or more than the second threshold TH2, the light emission intensity of the blue excitation light which has transmitted through the fluorescent substance without irradiation thereto increases, with respect to the case of the pulse P1. In contrast, an increasing rate of the light emission intensity of the yellow fluorescence excited by the blue excitation light with respect to the case of the pulse P1 is lower than that of the blue excitation light which has transmitted through the fluorescent substance without irradiation thereto. Therefore, the relative ratio between the emission intensity of the excitation light which has transmitted through the fluorescent substance without irradiation thereto and the emission intensity of the fluorescence emitted from the fluorescent substance, in one image pickup period, in the case of the pulse P1 differs from the relative ratio in the case of the pulse P2, i.e. the similarity between the spectrum of the illumination light in the case of the pulse P1 and the spectrum of the illumination light in the case of the pulse P2 is lost so that the color balance is lost.

As described above, when the pulse width of the PWM signal becomes not more than the first threshold TH1 or not less than the second threshold TH2, the color balance of the illumination light is lost, and therefore the endoscope apparatus 1 performs the color correction processing with respect to the video signal in the video signal processing section 23 of the processor 3.

Figure 4:
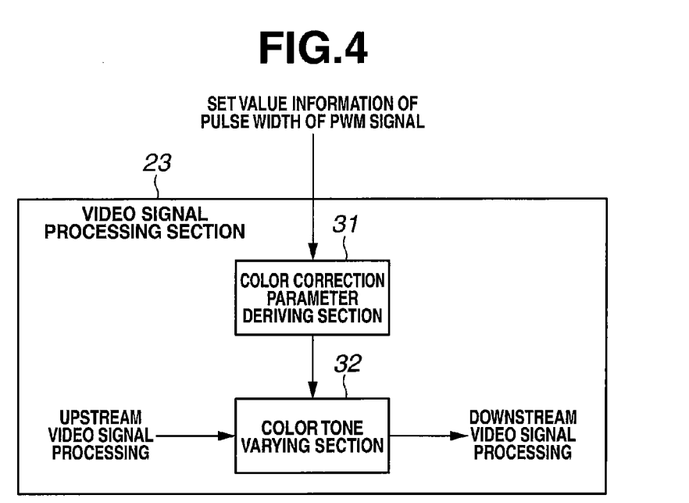
FIG. 4 is a configuration diagram showing a detailed configuration of a video signal processing section 23.

FIG. 4 is a configuration diagram showing a detailed configuration of the video signal processing section 23.

The video signal processing section 23 is configured to include a color correction parameter deriving section 31, a color tone varying section 32. Besides, in FIG. 4, the video signal processing section 23 is depicted to include only the color tone varying section 32 that performs the color correction, but there are provided a gamma correction section that performs the gamma correction, a separating section that separates a color signal component in the video signal and an enhance processing section that performs the enhance processing upstream or downstream of the color tone varying section 32.

The set value information of the pulse width of the PWM signal inputted from the light adjusting circuit 14 is inputted to the color correction parameter deriving section 31. The color correction parameter deriving section 31 stores functions showing relation between the pulse width of the PWM signal and correction parameters. When the set value information of the pulse width of the PWM signal is inputted to the color correction parameter deriving section 31, the color correction parameter deriving section 31 derives correction parameters in accordance with the set value of the pulse width, i.e. the driving time of the white LED 17, on the basis of the functions.

More specifically, since the color balance of the blue excitation light and the yellow fluorescence is lost when the pulse width of the PWM signal is not more than the first threshold TH1 or not less than the second threshold TH2, the color correction parameter deriving section 31 a correction parameter for B for correcting the video signal of blue (B), or correction parameters for R and G for correcting the video signal of yellow, i.e. red (R) and green (G). The correction parameters for B, or R and G thus derived are outputted to the color tone varying section 32.

The color tone varying section 32, as a color correction section, varies a gain of the video signal of B based on the correction parameter for B, or gains of the video signals of R and G based on the correction parameters for R and G to thereby perform the color correction. Hereinafter, a detailed configuration of the color tone varying section 32 will be described.

Figure 5:
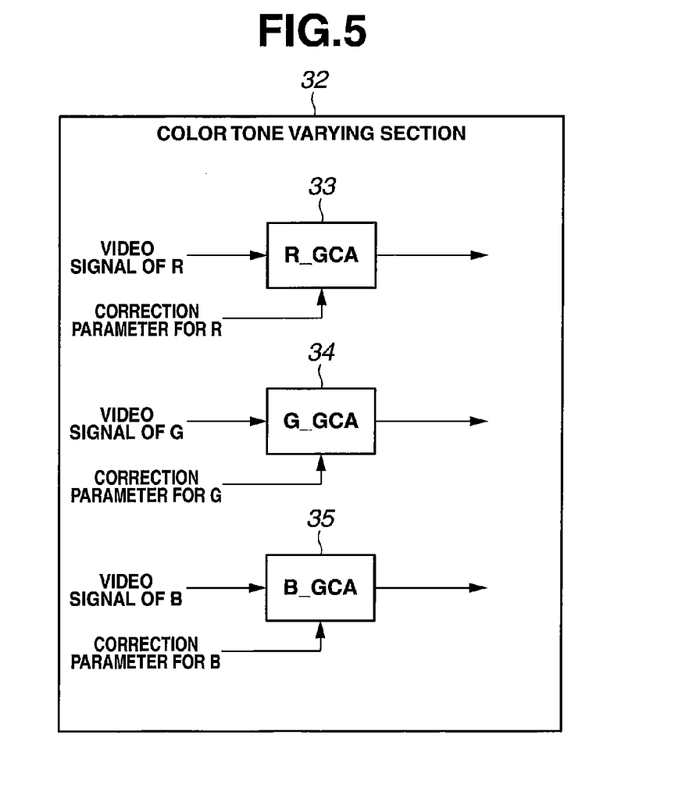
FIG. 5 is a configuration diagram showing a detailed configuration of a color tone varying section 32.

FIG. 5 is a configuration diagram showing a detailed configuration of the color tone varying section 32.

As shown in FIG. 5, the color tone varying section 32 is configured to include a gain control amplifier for correcting a gain of the video signal of R (hereinafter referred to as R_GCA) 33, a gain control amplifier for correcting a gain of the video signal of G (hereinafter referred to as G_GCA) 34 and a gain control amplifier for correcting a gain of the video signal of B (hereinafter referred to as B_GCA) 35.

Upstream of the color tone varying section 32, there is provided a separating section, not shown, that separates the input video signal into video signals of R, G and B. The video signal of R, the video signal of G and the video signal of B which are separated by the separating section are inputted to the R_GCA 33, the G_GCA 34 and the B_GCA 35, respectively. Further, the correction parameter for R, the correction parameter for G and the correction parameter for B which are derived by the color correction parameter deriving section 31 are inputted to the R_GCA 33, the G_GCA 34 and the B_GCA 35, respectively.

The R_GCA 33, the G_GCA 34 and the B_GCA 35 amplify or reduce the video signal of R, the video signal of G and the video signal of B with gains of the correction parameter for R, the correction parameter for G and the correction parameter for B, respectively.

For example, when the pulse width of the PWM signal is equal to or less than the first threshold TH1, the decreasing rate of the emission intensity of the blue excitation light is greater than the decreasing rate of the yellow fluorescence. Therefore, the color tone varying section 32 performs the color correction by amplifying the video signal of B with the gain of the correction parameter for B, or reducing the video signals of R and G with the gains of the correction parameters for R and G, respectively, when the pulse width of the PWM signal is equal to or less than the first threshold TH1.

Similarly, when the pulse width of the PWM signal is equal to or more than the second threshold TH2, the increasing rate of the emission intensity of the blue excitation light is greater than the increasing rate of the yellow fluorescence. Therefore, the color tone varying section 32 performs the color correction by reducing the video signal of B with the gain of the correction parameter for B, or amplifying the video signals of R and G with the gains of the correction parameters for R and G, respectively, when the pulse width of the PWM signal is equal to or more than the second threshold TH2.

Besides, in the case of performing the color correction by varying the gain of the video signal of B, the color tone varying section 32 may not provided with the R_GCA 33 and the G_GCA 34, and in the case of performing the color correction by varying the gains of the video signals of R and G, the color tone varying section 32 may not provided with the B_GCA 35.

Here, the color correction processing performed by the video signal processing section 23 thus configured will be explained. First, the case of performing the color correction by varying the gain of the video signal of B will be explained.

Figure 6:
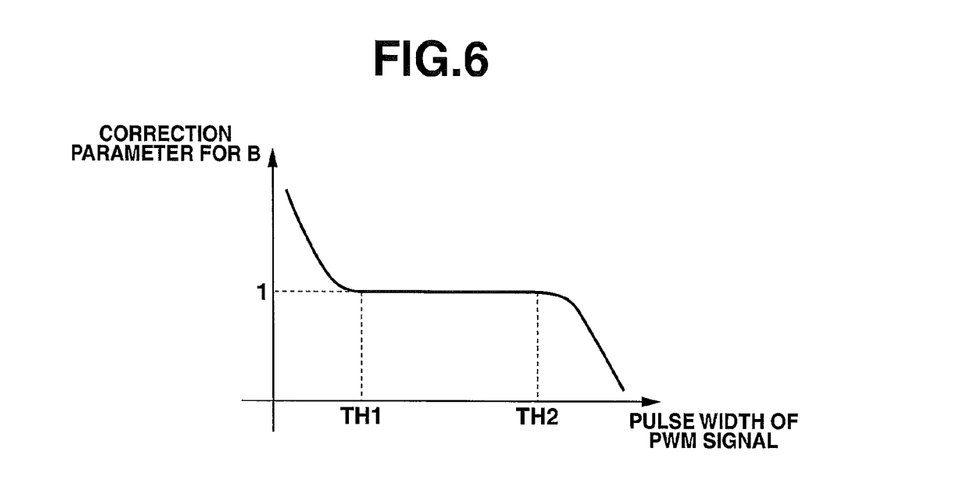
FIG. 6 is a graph showing a function of the pulse width of the PWM signal and a correction parameter for B.

FIG. 6 is a graph showing a function of the pulse width of the PWM signal and a correction parameter for B. As shown in the function of FIG. 6, when the pulse width of the PWM signal is wider than the first threshold TH1 and narrower than the second threshold TH2, the correction parameter for B is 1. When the pulse width of the PWM signal is equal to or less than the first threshold TH1, the correction parameter for B gradually increases to be greater than 1 as the pulse width becomes narrower. On the other hand, when the pulse width of the PWM signal is equal to or more than the second threshold TH2, the correction parameter for B gradually decreases to be smaller than 1 as the pulse width becomes wider.

When the set value information of the pulse width of the PWM signal is inputted to the color correction parameter deriving section 31 from the light adjusting circuit 14, the color correction parameter deriving section 31 derives the corresponding correction parameter for B according to the function of FIG. 6. That is, when the pulse width of the PWM signal is wider than the first threshold TH1 and narrower than the second threshold TH2, 1 is derived as the correction parameter for B. Further, when the pulse width of the PWM signal is equal to or less than the first threshold TH1, a value greater than 1 is derived as the correction parameter for B, and when the pulse width of the PWM signal is equal to or more than the second threshold TH2, a value smaller than 1 is derived as the correction parameter for B. The correction parameter thus derived is inputted to the B_GCA 35 of the color tone varying section 32. Besides, the color correction parameter deriving section 31 may store a table in which the pulse width of the PWM signal and the correction parameter for B are related, instead of the function of FIG. 6, and derive the correction parameter for B in accordance with the pulse width.

When the pulse width of the PWM signal is wider than the first threshold TH1 and narrower than the second threshold TH2, 1 is inputted to the B_GCA 35 as the correction parameter for B. The B_GCA 35 outputs the inputted video signal of B as it is, with the gain multiplied by one, i.e. without changing the gain.

Further, when the pulse width of the PWM signal is equal to or less than the first threshold TH1, the value greater than 1 is inputted to the B_GCA 35. The B_GCA 35 amplifies the gain of the inputted video signal of B according to the value greater than 1.

On the other hand, when the pulse width of the PWM signal is equal to or more than the second threshold TH2, the value smaller than 1 is inputted to the B_GCA 35. The B_GCA 35 reduces the gain of the inputted video signal for B according to the value smaller than 1.

Besides, in the case of performing the color correction by varying the gain of the video signal of B, 1 is inputted to the R_GCA 33 and also the G_GCA 34 as the correction parameters so as not to vary the gains of the video signals for R and G. Alternatively, it may be configured that the R_GCA 33 and the G_GCA 34 are not provided in the color tone varying section 32.

Next, a case of performing the color correction by varying the gains of the video signals of R and G will be explained.

Figure 7:
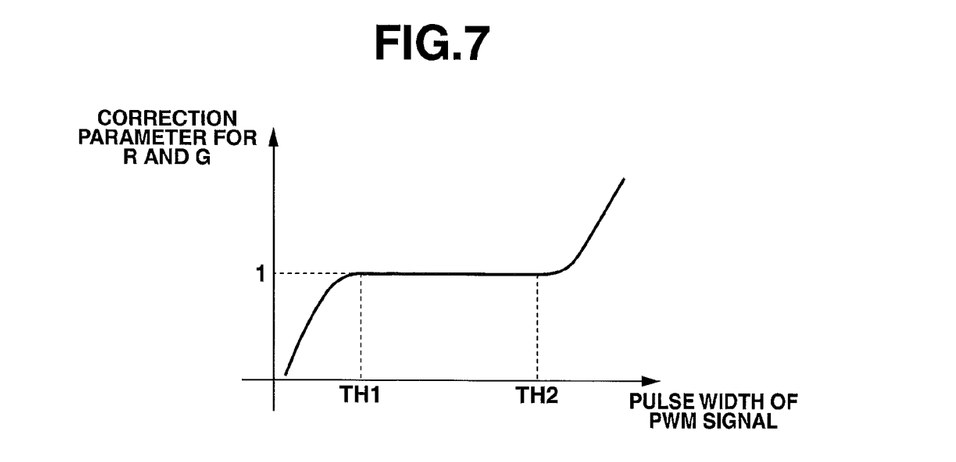
FIG. 7 is a graph showing a function of the pulse width of the PWM signal and a correction parameter for R and G.

FIG. 7 is a graph showing a function of the pulse width of the PWM signal and the correction parameter for R and G. As shown in the function of FIG. 7, when the pulse width of the PWM signal is wider than the first threshold TH1 and narrower than the second threshold TH2, the correction parameter for R and G is 1. When the pulse width of the PWM signal is equal to or less than the first threshold TH1, the correction parameter for R and G gradually decreases to be smaller than 1 as the pulse width becomes narrower. On the other hand, when the pulse width of the PWM signal is equal to or more than the second threshold TH2, the correction parameter for R and G gradually increases to be greater than 1 as the pulse width becomes wider.

When the set value information of the pulse width of the PWM signal is inputted to the color correction parameter deriving section 31 from the light adjusting circuit 14, the color correction parameter deriving section 31 derives the corresponding correction parameter for R and G according to the function of FIG. 7. That is, when the pulse width of the PWM signal is wider than the first threshold TH1 and narrower than the second threshold TH2, 1 is derived as the correction parameter for R and G. Further, when the pulse width of the PWM signal is equal to or less than the first threshold TH1, a value smaller than 1 is derived as the correction parameter for R and G, and when the pulse width of the PWM signal is equal to or more than the second threshold TH2, a value greater than 1 is derived as the correction parameter for R and G. The correction parameter thus derived is inputted to the R_GCA 33 and also the G_GCA 34 of the color tone varying section 32. Besides, the color correction parameter deriving section 31 may store a table in which the pulse width of the PWM signal and the correction parameter for R and G are related, instead of the function of FIG. 7, and derive the correction parameter for R and G in accordance with the pulse width.

When the pulse width of the PWM signal is wider than the first threshold TH1 and narrower than the second threshold TH2, 1 is inputted to the R_GCA 33 and also the G_GCA 34 as the correction parameter for R and G. The R_GCA 33 and the G_GCA 34 output the inputted video signals of R and G as they are, with the gains multiplied by one, i.e. without changing the gains.

Further, when the pulse width of the PWM signal is equal to or less than the first threshold TH1, the value smaller than 1 is inputted to the R_GCA 33 and also the G_GCA 34. The R_GCA 33 and the G_GCA 34 reduce the gains of the inputted video signals of R and G, respectively, according to the value smaller than 1.

On the other hand, when the pulse width of the PWM signal is equal to or more than the second threshold TH2, the value greater than 1 is inputted to the R_GCA 33 and also the G_GCA 34. The R_GCA 33 and also the G_GCA 34 amplify the gains of the inputted video signals for R and G, respectively, according to the value greater than 1.

Besides, in the case of performing the color correction by varying the gains of the video signals of R and G, 1 is inputted to the B_GCA 35 as the correction parameter so as not to vary the gain of the video signal for B. Alternatively, it may be configured that the B_GCA 35 is not provided in the color tone varying section 32.

In the present embodiment, the explanation is made with respect to the case where the color correction is performed by varying the gain of the video signal of B, or varying the gains of the video signals of R and G. However, the color correction may be performed by varying the gains of the video signals of R, G and B. For example, when the pulse width of the PWM signal is equal to or less than the first threshold TH1, the color correction is performed by amplifying the gain of the video signal of B and reducing the gains of the video signals of R and G so that appropriate color balance is obtained. When the pulse width of the PWM signal is equal to or more than the second threshold TH2, the color correction is performed by reducing the gain of the video signal of B and amplifying the gains of the video signals of R and G so that appropriate color balance is obtained.

As described, the endoscope apparatus 1 is configured such that the correction parameter is derived in accordance with the pulse width of the PWM signal, i.e. the driving time of the white LED 17 in the color correction parameter deriving section 31. Further, the endoscope apparatus 1 is configured such that, when the color balance of the illumination light is lost due to the driving time of the white LED 17, the color correction of the video signal with correction parameter in accordance with the driving time.

Thus, according to the endoscope apparatus of the present embodiment, if the color balance is changed by the light adjustment of the light source, the appropriate color balance can be maintained.

The present invention is not limited to the foregoing embodiments, and various modification and alternations are possible within a rage where the gist of the present invention is not changed.

What is claimed is:

1. An endoscope apparatus comprising:
   a light source section that includes a semiconductor light source that emits excitation light and a fluorescent substance that emits fluorescence by being excited by the excitation light, and emits synthesized light of the excitation light and the fluorescence as illumination light;
   an image pickup section that picks up an image of an observation part illuminated by the illumination light;
   a video signal processing section that converts an image pickup signal outputted by the image pickup section to a video signal;
   a light adjusting circuit that generates setting value information having a pulse width for causing the semiconductor light source to emit light, based on a luminance signal outputted from the video signal processing section; and a light source control section that adjusts driving time of the semiconductor light source in each image pickup period of the image pickup section based on the setting value information inputted from the light adjusting circuit;

wherein the video signal processing section includes:

a color correction parameter deriving section that derives a first color correction parameter for correcting a gain of a color component signal related to the excitation light of the video signal, and a second color correction parameter, which is different from the first color correction parameter, for correcting a gain of a color component signal related to the fluorescence, based on the setting value information and on a threshold defined in advance as a limit value of a driving time of the semiconductor light source in which appropriate color balance is maintained based on a relation between the driving time of the semiconductor light source and color balance of illumination light; and a color correcting section that corrects the gain of the color component signal related to the excitation light of the video signal with the first color correction parameter, and corrects the gain of the color component signal related to the fluorescence with the second color correction parameter.

2. The endoscope apparatus according to claim 1, wherein the color correction parameter deriving section compares the setting value information with a first threshold which represents a lower limit value of the driving time of the semiconductor light source in which appropriate color balance is maintained based on the relation between the driving time of the semiconductor light source, as the threshold, and color balance of illumination light, and when the driving time of the semiconductor light source, which is represented by the setting value information, is shorter than the first threshold, the color correction parameter deriving section derives the first color correction parameter such that the gain of the color component signal related to the excitation light increases and derives the second color correction parameter such that the gain of the color component signal related to the fluorescence decreases, as the driving time of the semiconductor light source is shortened.

3. The endoscope apparatus according to claim 2, wherein the color correction parameter deriving section further compares the setting value information with a second threshold which is greater than the first threshold and which represents an upper limit value of the driving time of the semiconductor light source in which appropriate color balance is maintained based on the relation between the driving time of the semiconductor light source and color balance of illumination light, and when the driving time of the semiconductor light source, which is represented by the setting value information, is longer than the second threshold, the color correction parameter deriving section derives the first color correction parameter such that the gain of the color component signal related to the excitation light decreases and derives the second color correction parameter such that the gain of the color component signal related to the fluorescence increases, as the driving time of the semiconductor light source is lengthened.

4. The endoscope apparatus according to claim 3, wherein, when the driving time of the semiconductor light source, which is represented by the setting value information, is longer than the first threshold and shorter than the second threshold, the color correction parameter deriving section derives the first and second color correction parameters such that the gain of the color component signal related to the excitation light is equal to the gain of the color component signal related to the fluorescence.

5. The endoscope apparatus according to claim 1, wherein the semiconductor light source is an LED or a laser diode.

* * * * *